(12) United States Patent
Cheng et al.

(10) Patent No.: US 7,863,044 B2
(45) Date of Patent: Jan. 4, 2011

(54) P18 IN STEM CELL MANIPULATIONS

(76) Inventors: Tao Cheng, 1529 Brimfield Dr., Sewickley, PA (US) 15143; Youzhong Yuan, 475 Sage Dr., Pittsburgh, PA (US) 15243; Hongmei Shen, 1529 Brimfield Dr., Sewickley, PA (US) 15143; Hui Yu, 4910 Centre Ave., Apt. E7, Pittsburgh, PA (US) 15213; David T. Scadden, 62 Lexington St., Weston, MA (US) 02493

( * ) Notice: Subject to any disclaimer, the term of this patent is extended or adjusted under 35 U.S.C. 154(b) by 473 days.

(21) Appl. No.: 10/576,785

(22) PCT Filed: Oct. 25, 2004

(86) PCT No.: PCT/US2004/035220
§ 371 (c)(1),
(2), (4) Date: Apr. 21, 2006

(87) PCT Pub. No.: WO2005/046581
PCT Pub. Date: May 26, 2005

(65) Prior Publication Data
US 2007/0081981 A1 Apr. 12, 2007

Related U.S. Application Data

(60) Provisional application No. 60/514,329, filed on Oct. 24, 2003, provisional application No. 60/620,154, filed on Oct. 19, 2004.

(51) Int. Cl.
*C12N 15/00* (2006.01)
(52) U.S. Cl. .................. 435/377; 435/455; 435/461
(58) Field of Classification Search .................. None
See application file for complete search history.

(56) References Cited

U.S. PATENT DOCUMENTS 5,837,507 A * 11/1998 Largman et al. ......... 424/93.21
6,033,847 A * 3/2000 Sherr et al. .............. 435/6

OTHER PUBLICATIONS

Franklin et al, Genes and Development, 1998, vol. 12, No. 18, pp. 2899-2911.*
Deans et al, "Mesenchymal Stem Cells: Biology and potential clinical uses" Experimental Hematology, 2000, vol. 28, pp. 875-884.*
Nakauchi et al, "Quantitative Assessment of the Stem Cell Self-Renewal Capacity" Annals of the New York Academy of Sciences, 2001, vol. 938, pp. 18-25.*
Guan et al, "Growth suppression by p18, a p16(INK4/MTS1) and p14(INK4B/MTS2)-related CDK6 inhibitor, correlates with wild-type pRb function" Genes and Development, 1994, vol. 8, No. 24, pp. 2339-2952.*
Cheng, T "Toward 'SMART' Stem cells" Gene Therapy, 2008, vol. 15, pp. 67-73.*
Bertrand et al, "Comparison of antisense oligonucleotides and siRNAs in cell culture and in vivo" Biochemical and Biophysical Research Communications, 2002, vol. 296, pp. 1000-1004.*
An et al, "Efficient Lentiviral Vectors for Short Hairpin RNA delivery into Human Cells" Human Gene Therapy, Aug. 2003, vol. 14, pp. 1207-1212.*
Walters et al, "The Effectiveness of Double-Stranded Short Inhibitory RNAs (siRNAs) May Depend on the Method of Transfection" Antisense and Nucleic Acid Drug Development, 2002, vol. 12, pp. 411-418.*
David S. Franklin, Viriginia L. Godfrey, Hayyoung Lee, Grigoriy I. Kovalev, Robert Schoonhoven, Selina Chen-Kiang, Lishan Su and Yue Xiong, *CDK Inhibitors $p18^{INK4c}$ and $p27^{Kip1}$ Mediate Two Separate Pathways To Collaboratively Suppress Pituitary Tumorigenesis*, Genes & Development 12, (18) 2899-2911 (1998).
M.P. Tschan, U.R. Peters, J.F. Cajot, D.C. Betticher, M.F. Fey, and A. Tobler, *The Cyclin-Dependent Kinase Inhibitors $p18^{INK4c}$ and $p19^{INK4d}$ Are Highly Expressed In CD34+ Progenitor and Acute Myeloid Leukaemic Cells But Not In Normal Differentiated Myeloid Cells*, British Journal of Haematology, 644-651, (1999).
Shi-Jiang Lu, Chengshi Quan, Fei Li, Loyda Vida and George R. Honig, *Hematopoietic Progenitor Cells Derived From Embryonic Stem Cells: Analysis Of Gene Expression*, Stem Cells 20, 428-437, (2002).
Youzhong Yuan, Hongmei Shen, David S. Franklin, David T. Scadden and Tao Cheng, *In Vivo Self-Renewing Divisions Of Haematopoietic Stem Cells Are Increased In The Absence Of The Early G1-Phase Inhibitor, $p18^{INK4c}$*, Nature Cell Biology, vol. 6, No. 5, 436-442 (2004).

(Continued)

*Primary Examiner*—Allison M Ford
(74) *Attorney, Agent, or Firm*—K&L Gates LLP

(57) ABSTRACT

A method to increase self-renewal of an undifferentiaded human stem cell culture or cell line, by reducing or eliminating the presence of the protein "p18".

15 Claims, 18 Drawing Sheets

OTHER PUBLICATIONS

Tao Cheng, et al., Transforming growth factor B1 mediates cell-cycle arrest of primitive hematopoietic cells independent of p21$^{Cip1/Waf1}$ or P27$^{Kip1}$, Blood, Dec. 15, 2001, vol. 98, No. 13, pp. 3643-3649.

* cited by examiner

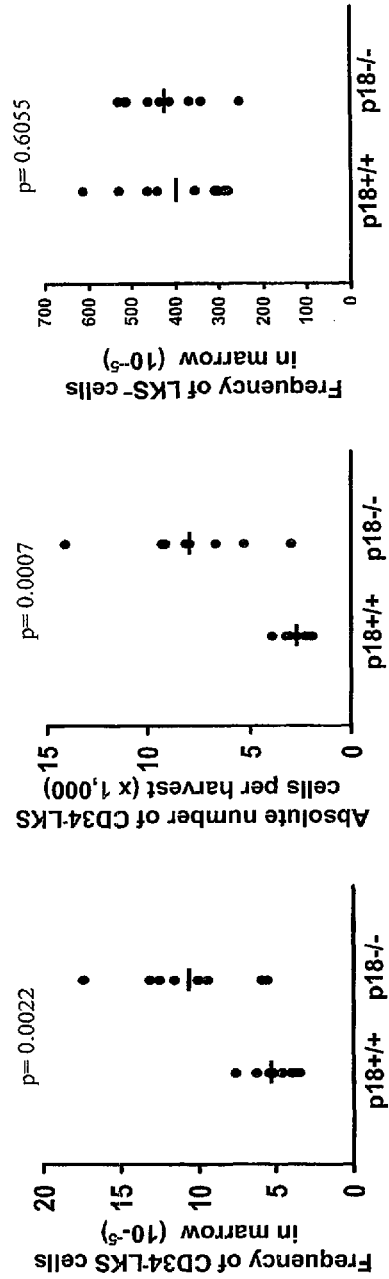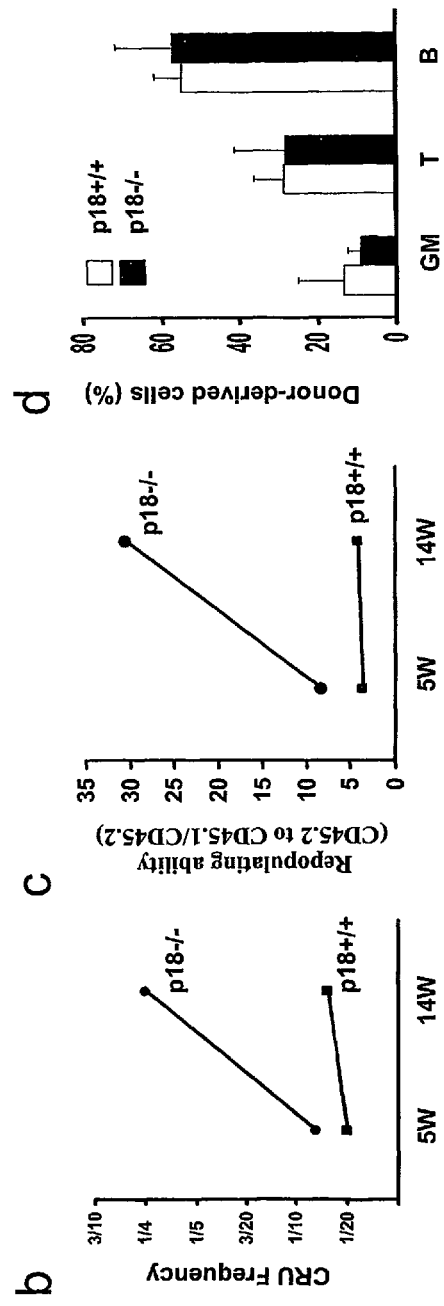
Fig. 3

There is no increase of BrdU incorporation in p18-/- hematopoietic cell subsets from non-transplanted (month 0) or transplanted (month 2, 4, 5) animals

Fig. 7 A similar proliferative rate between p18+/+ and p18-/- genotypes during 3-day culture after single CD34-LKS cells from non-transplanted mice were plated A similar proliferative rate between p18+/+ and p18-/- genotypes during 3-day culture after single CD34-LKS cells from transplanted mice (2 months post transplant) were plated

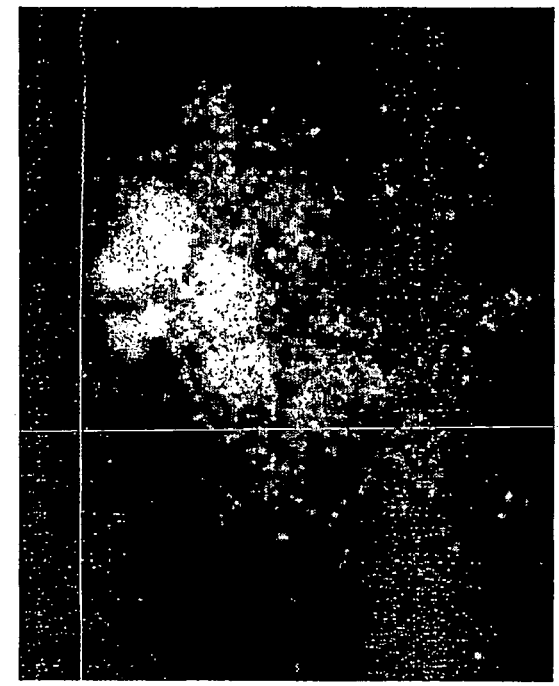
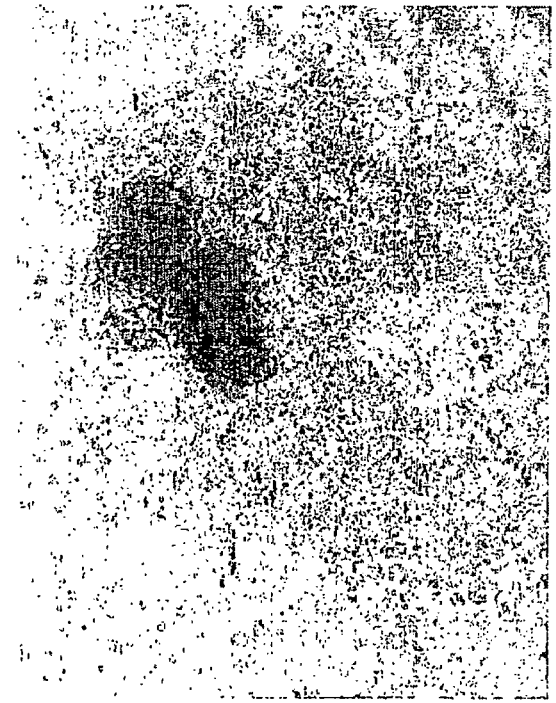
Fig. 14

P18 IN STEM CELL MANIPULATIONS

RELATED APPLICATIONS

This application claims priority from Tao CHENG, provisional patent application Ser. No. 60/514,329 (filed 24 Oct. 2003), and from Tao CHENG, provisional patent application Ser. No. 60/620,154 (filed 19 Oct. 2004), the contents of which are incorporated by reference here.

GOVERNMENT INTEREST

Certain claims of this application may have been reduced to practice using National Institutes of Health grant numbers DK02761-01 and/or HL70561.

BACKGROUND

Stem cells (for example, hematopoietic stems cells, or "HSCs") provide many potential therapeutic uses in vivo. Stem cells' ability to differentiate into a variety of mature cell types indicates that undifferentiated stem cells may be clinically useful, for example, in treating disease both malignant (e.g., chronic myelogenous leukemia, acute myelogenous leukemia) and non-malignant (e.g., severe aplastic anemia, inherited metabolic disorders). A problem in using human stem cells in vivo, however, is that while stem cells may differentiate into a variety of mature cell types, the lifespan of a specific human stern-cell cell culture is limited by the cell line's ability to "self-renew" or propagate new undifferentiated stem cells (called "self-renewal"). Thus, the art has sought a way to increase the lifespan of human stem cell cultures or cell lines, by increasing self-renewal.

SUMMARY

I have found a way to increase human-compatible stem cell self-renewal. My invention involves reducing or eliminating the presence of the protein "p18" in the undifferentiated stem cell culture. This may be done, for example, by downregulating expression of the p18 gene, or by attacking the p18 polypeptide with an enzyme or chemical.

The protein "p18" (p18$^{INK4C}$, INK4C, Cdlcn2c) is known in the art. See e.g., H. HIRAI et al., "Novel INK4 proteins, p19 and p18, are specific inhibitors of the cyclin D-dependent kinases CDK4 and CDK6", 15(5) MOL. CELL. BIOL. 2672 (1995) (disclosing primary amino acid sequence of mouse p18); K. L. GUAN et al., "Growth suppression by p18, a p16INK4/MTS1- and p14INK4B/MTS2-related CDK6 inhibitor, correlates with wild-type pRb function," 8(24) GENES DEV. 2939 (1994) (disclosing primary amino acid sequence of human p18). p18 is a cyclin-dependent kinase inhibitor (CKI). P18 is an INK4 family protein. It acts at the early G1-phase of the cell cycle.

p18 has a unique role in inhibiting self-renewal of hematopoietic stem cells (HSCs) in vivo. Increased stem cell self-renewal might be readily achieved in vitro due to the absence of p18. To demonstrate this, we first performed the Dexter long-term culture of bone marrow cells. This enumerates the cobble stone area-forming cell (CAFC). This is an in vitro surrogate for murine HSC.

There was no difference of CAFC yield in the first 4 weeks of the long-term culture between p18−/− (the genotype for cells lacing the p18 gene) and p18+/+ flasks. However, significantly more CAFCs were constantly generated in p18−/− than in p18+/+ flasks (p<0.01, n=4) from 6 weeks to 19 months after the initial culture. Strikingly, the frequency of CAFC at week 19 in p18−/− culture was still equivalent to its level at week 5, whereas the p18+/+ culture nearly lost its ability of producing CAFCs at week 19. In addition, the higher production of CAFCs in p18−/− culture was also associated with a higher production of non-adherent cells, which were dominated by differentiated cells in myeloid lineage.

This hints that the difference was due to the intrinsic deficiency of p18 in HSCs, but does not confirm it. To confirm it, irradiated stromal cells from wild type bone marrow were used instead in the long-term culture with limiting dilution of the input cells from p18−/− or p18+/+ marrow. Using these cells, there was 2-fold increase of CAFC frequency (week 5-6) in p18−/− plates compared to the p18+/+ plates.

To further assess HSC proliferation in a defined population, we examined in vitro cell divisions of the highly purified HSCs, namely the CD34$^-$Lin$^-$c-Kit$^+$Sca-1$^+$ (CD34$^-$LKS) cells. The repopulating ability of the sorted CD34$^-$LKS cells (CD45.2) was validated by the limiting dilution assay for competitive repopulating unit (CRU) in the congenic (CD45.1) mice. Three months after transplantation, we were able to determine approximately one CRU in 20 CD34$^-$LKS cells from p18+/+ marrow and one CRU in 10 CD34$^-$LKS cells from the p18−/− marrow examined. Single CD34$^-$LKS cells were deposited to Terasaki plates (one cell/well) and cultured in serum free medium supplemented with SCF, Flt3L and TPO. While most cells entered cell cycle within 3 days, which was in agreement with previous studies by others, surprisingly, there was no significant difference of the rate of cell division between p18−/− and p18+/+ CD34$^-$LKS cells (>100 cells/experiment, 5 experiments).

This indicates that p18 deficiency does not increase the proliferative rate of HSC. Rather. P18 deficiency may modulate the fate-choice of HSC toward symmetric cell divisions. To directly test this hypothesis, single CD34-KSL cells were cultured for two days and paired daughter cells along with minimal Sca-1 depleted competitor cells (CD45.1/2 F1) were separately transplanted into different recipients. Positive engraftment was found in the single daughter HSC transplanted mice.

Together, these findings suggest that p18 deficiency favors symmetric divisions in the compartment of HSC though a cell-cycle independent manner. Down modulating p18 may pen-nit enhanced stem cell expansion in vitro, a method that can be used in stem cell expansion and in defining other active agents for stem cell expansion. Given the nonspecific expression of p18 in hematopoietic cells, this approach can also be applied to other stem cell types in the body.

BRIEF DESCRIPTION OF THE FIGURES

FIG. 1a further demonstrates a standardization based on the correlation between the relative intensity of p18−/− signal in total and the percentage of p18−/− cells in the mixed population.

FIG. 3a demonstrates the frequency and absolute number of CD34-LKS cells in marrow of p18+/+ mice compared to p18−/− mice.

FIG. 3b demonstrates increased competitive reconstitution units (CRU) of p18+/+HSCs compared to p18−/− HSCs at 5 weeks (5W) and 14 weeks (14W).

FIG. 3c demonstrates the repopulating ability of the test cells as determined by the ratios of CD45.2 to CD45.1/CD45.2 cells in blood at 5 weeks (5W) and 14 weeks (14W) after transplantation in p18+/+ mice compared to p18−/− mice.

FIG. 3d demonstrates the percentage of donor-derived cells in multiple lineages (GM, T, B) of p18+/+ and p18−/− cells.

FIG. 12a shows a Western analysis for p18 protein. NS: negative control with non-specific RNA oligos; p18 siRNA: cells treated with a specific sequence of p18 small interfering RNA oligos; NT: negative control without treatment. FIG. 12b shows a summary of multiple experiments, showing 70% of p18 protein can be removed by p18 siRNA in two days.

FIG. 14 shows a successful example of delivering p18 siRNA into human stem cells by an alternative lentiviral method. The green color is an indicator for the p18 siRNA presence in the cells.

DETAILED DESCRIPTION

Stem cells in vivo have a unique ability to reproduce themselves (self-renewal or self-regeneration) in physiologically determined balance with differentiation or cell death. Cell cycle regulation is one of the fundamental mechanisms underlying cell fate determination. Emerging data indicate that cell cycle status per se is a critical determinant of stem or progenitor cell function, but molecular events orchestrating these deterministic roles are largely undefined. In mammalian cells, entry into the cell cycle requires sequential activation of the cyclin-dependent kinases (CDK) 4/6 and CDK2, which are inhibited by the INK4 proteins ($p16^{INK4A}$, $p15^{INK4B}$, $p18^{INK4C}$, and $p19^{INK4D}$) and the Cip/Kip proteins ($p21^{Cip1/Waf1}$, $p27^{kip1}$ and $p57^{Kip2}$), respectively.

Both INK4 and Cip/Kip families compose an important class of cell cycle inhibitors, termed CDK inhibitors (CKIs). While a complex array of extracellular signals and intracellular transduction pathways participate in communicating cell cycle regulatory cues, CKIs appear to be critical mediators of cell cycle control that may function in a cell autonomous manner. As previously shown in murine hematopoietic cells, p21 deficiency resulted in an enlarged hematopoietic stem cell (HSC) pool under homeostasis, but stem cell function was compromised in stress conditions. Given that the two CKI families target distinct components in the cell cycle machinery, we hypothesized that the INK4 proteins functioning earlier in G1 may influence the fate of stem cell division upon mitogenic stimuli in a unique manner. This hypothesis was indirectly supported by recent studies indicating $p16^{INK4A}$ and $p19^{ARF}$ as downstream mediators of the Bmi-1 protein regulating HSC self-renewal. The distinct INK4 family member $p18^{INK4C}$ is expressed in multiple tissue types including hematopoietic cells, the loss of which in mice results in organomegaly with higher cellularity and increases the incidence of tumorigenesis with advanced age or in the presence of carcinogens. We now report an inhibitory role of p18 in HSC self-renewal through the use of reconstituted mice with p18 deficient hematopoietic cells and extensive in vivo evaluation of stem cell function.

Figure 1:
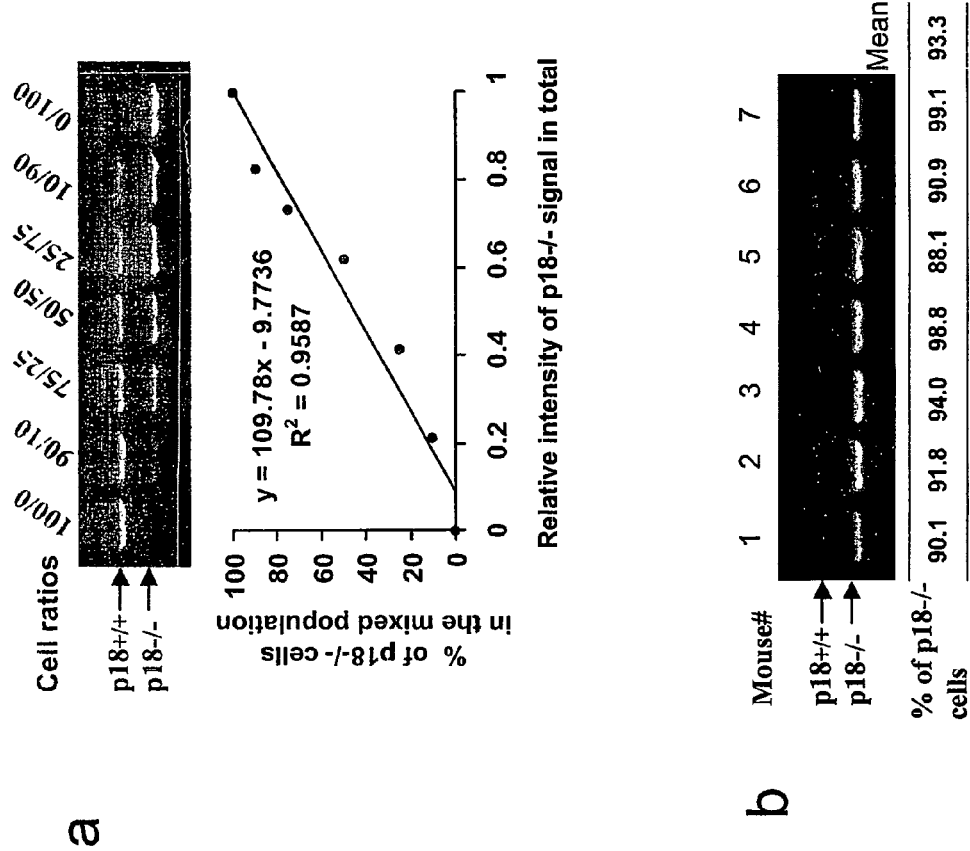
FIG. 1a demonstrates a semi-quantitative PCR performed on bone marrow cells from p18+/+ mice and p18−/− mice that were mixed at different cell ratios.
FIG. 1b demonstrates the converted percentages of p18−/− cells in the blood.

Hematopoietic stem cells are responsible for long-term hematopoietic reconstitution of irradiated mice and their functions can be definitively examined in transplant models. We first took the approach of competitive bone marrow transplantation to directly assess the possible impact of p18 absence on hematopoietic reconstitution. Our data is shown in FIG. 1.

Figure 16:
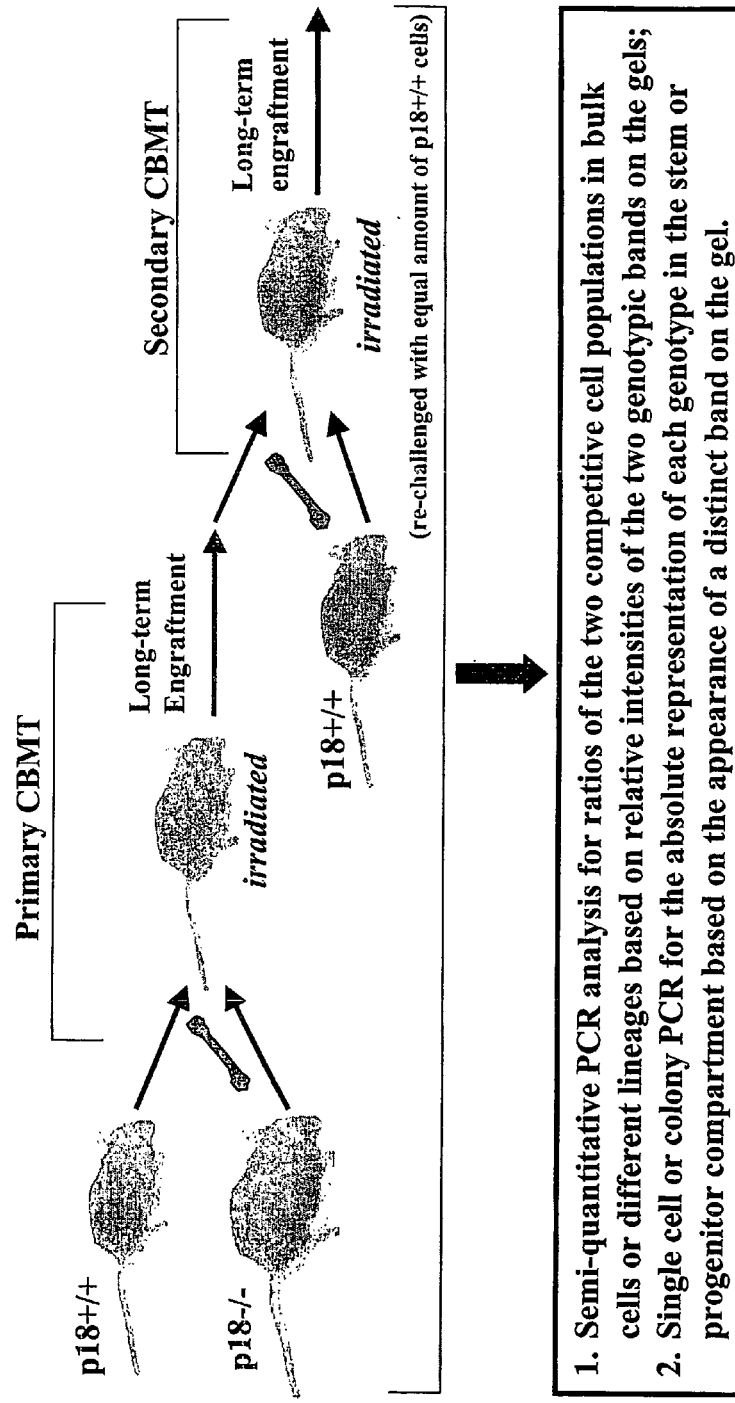
FIG. 16 shows the experimental procedure for competitive bone marrow transplantation (cBMT) coupled with serial transfer as extensively used in FIGS. 1 and 2.

FIG. 16 shows a schematic diagram of "Competitive and Serial Bone Marrow Transplantation." The competitive bone marrow transplantation ("CBMT") is performed repeatedly (serially).

In FIG. 16, equal numbers ($2\times10^6$) of bone marrow nucleated cells from p18+/+ mice and p18−/− mice were co-transplanted into lethally irradiated recipients. The relative contribution from each genotype was quantified with a semi-quantitative PCR approach. Based on the standardization simultaneously generated under identical PCR conditions (see FIG. 1a), p18−/− blood cells constituted 93.3% (vs. 6.7% of p18+/+ genotype on average) in the mixed populations. Therefore, there was on average a 14-fold greater abundance of the long term repopulating ability (LTRA) in p18−/− bone marrow cells compared with the same number of p18+/+ marrow cells.

To determine whether the increased engraftment of the p18−/− genotype cells occurred at the HSC or the hematopoietic progenitor cell (HPC) level, quantitative assays for colony forming cell (CFC) (in vitro surrogate for HPC) and long-term culture initiating cell (LTC-IC) (in vitro surrogate for HSC), were performed with subsequent colony genotypic analyses by PCR. Dramatic overrepresentation of the p18−/− genotype was observed in both the CFC and LTC-IC pools. This data is shown in Table 1.

TABLE 1

Follow-up of p18−/− genotype in individual stem/progenitor cells after CBMT

|  |  | A | B | C | D | E | F | G |
|---|---|---|---|---|---|---|---|---|
| Primary CBMT | Exp. 1 | CFC | 10 | 3 | 39 | 38 | 1 | 97.5 |
|  | Exp. 2 | CFC | 7 | 3 | 122 | 115 | 7 | 94.3 |
|  |  |  | 10 | 3 | 108 | 107 | 1 | 99.1 |
|  |  |  | 14 | 3 | 144 | 143 | 1 | 99.3 |
|  |  | LTC-IC | 10 | 3 | 48 | 45 | 3 | 93.7 |
|  | Exp. 3 | CFC | 8 | 3 | 85 | 72 | 13 | 80.0* |
|  |  |  | 12 | 3 | 122 | 110 | 12 | 90.1* |
|  |  | LKS | 12 | 2 | 220 | 201 | 19 | 91.4 |
| Secondary CBMT** |  | CD34− LKS | 12 or 22*** | 3 | 109 | 101 | 8 | 92.7 |

Legend:
Column A: Clonal Culture
Column B: Months After Bone Marrow Transplant
Column C: Number of mice analyzed
Column D: Total number of colonies analyzed
Column E: Total number of p18−/− colonies shown
Column F: Total number of p18+/+ colonies shown
Column G: p18−/− dominance (as a percentage of the total colonies shown)

In addition, we found that 91.4% of the Lin−c-kit+Sca-1+ cells (LKS) (an in vivo immunophenotype enriched for HSCs) were also of the 18−/− genotype 12 months after the competitive bone marrow transplant (Table 1). These data indicate that p18−/− hematopoietic cells including the primitive HSCs have a strong competitive advantage over wild type cells.

To test whether the enhanced engraftment was attributed to increased self-renewal of hematopoietic cells in the absence of p18, serial transplantation was integrated with the competitive bone marrow transplant assay. We collected bone marrow cells from mice 10 months after the primary competitive bone marrow transplant and performed a secondary competitive bone marrow transplant. Bone marrow nucleated cells from the primarily transplanted mice were rechallenged with an equal amount ($2\times10^6$) of marrow nucleated cells newly isolated from p18+/+ animals at 8 weeks of age.

Strikingly, the p18−/− hematopoietic cells were still able to outcompete the co-transplanted p18+/+ cells and became dominant again in the new recipients 8-12 months following the secondary competitive bone marrow transplant. These results are shown in FIG. 2.

Figure 2:
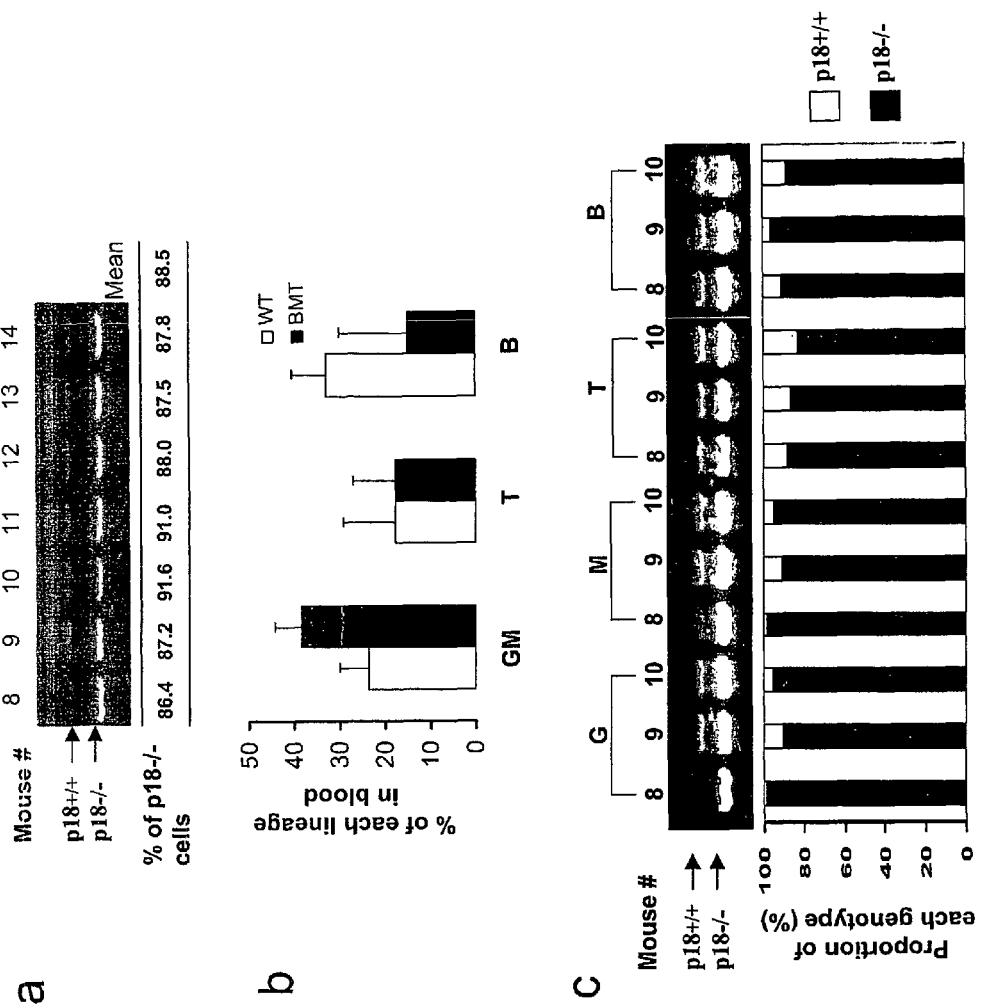
FIG. 2a demonstrates a semi-quantitative PCR performed after secondary competitive bone marrow transplantation (cBMT).
FIG. 2b demonstrates percentages of each lineage in blood for transplanted mice (BMT) compared to non-transplanted mice (WT).
FIG. 2c demonstrates semi-quantitative PCR for genotypic analysis of each lineage in p18+/+ and p18−/− mice.

FIG. 2 shows sustained multipotentiality and dominance of the regenerated p18−/− HSCs after secondary competitive bone marrow transplant. Bone marrow cells firm the mice at 10 months after primary competitive bone marrow transplant were mixed with freshly isolated bone marrow cells from non-transplanted wild type mice at age of 8 weeks at a 1:1 ratio and secondarily transplanted into lethally irradiated wild-type recipients ($4\times10^6$ cells in total/mouse). Semi-quantitative PCR was again performed for blood cells drawn from the mice after secondary competitive bone marrow transplant. FIG. 2a shows representative data for the blood cells collected at 8 months after secondary competitive bone marrow transplant. In FIG. 2a, columns numbered 8 to 14 identify the seven individual mice used. The same standardization curve as shown in FIG. 1a was used for this analysis since both batches of DNA samples were amplified at the same time under identical conditions. FIG. 2b shows a lineage differentiation profile. Marrow cells from the mice (number 8, 9 and 10) 12 months after secondary competitive bone marrow transplant were stained with lineage markers for granulocytes (G), monocytes (M), T cells (T) or B cells (B) and each lineage was sorted for genotypic analysis with the semi-quantitative PCR method as described in FIG. 1.

FIG. 2a shows that the LTRA of the p18−/− hematopoietic cells assessed in the secondary recipients remained on average 8-fold greater than that of the p18+/+ cells. FIG. 2b shows that the flow cytometric analysis of blood and bone marrow cells from the secondary recipient mice revealed no predominant growth of a specific lineage as compared to the non-transplanted wild type mice.

To further characterize the breadth of cell types repopulated by the p18−/− cells, immunophenotypically defined cell types from different lineages were sorted from the marrow at 12 months after the secondary competitive bone marrow transplant, and tested for the genotypic ratios. Similar to what was found with whole blood cells, the dominance of the p18−/− phenotype was observed in all major blood cell types (FIG. 2c). These data indicate persistence of regenerated cells with multilineage differentiation potential (HSCs) in secondary recipients.

Stem cell concentration tends to decrease with serial bone marrow transplantation and we previously observed premature exhaustion of HSCs in the absence of p21. To test whether the p18−/− HSCs manifest the same outcome, we isolated one of the most primitive phenotypes for murine HSCs in vivo, the CD34−LKS cells from the mice at 12 months after the secondary competitive bone marrow transplant and determined their genotypic characteristic at the single cell level. These results are shown in Table 1.

Figure 17:
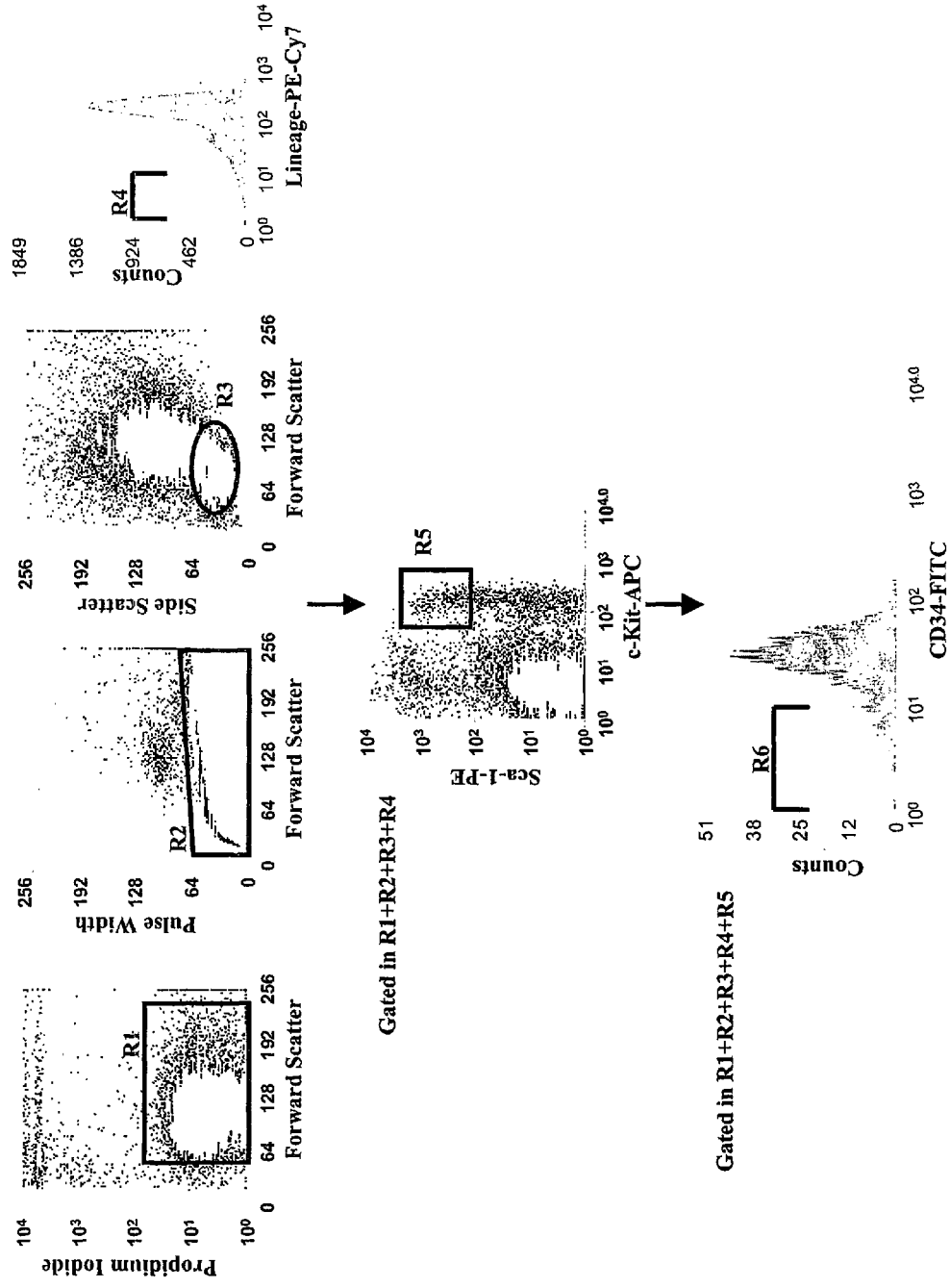
FIG. 17 shows the procedure of isolating the hematopoietic stem cells by immuno-staining and flow cytometry cell sorter.

FIG. 17 shows sorting strategies for the stem cells with the immunophenotype, CD34−LKS. To isolate the most primitive stem cells, we first exclude the mature cell populations, then enrich the cells with Sca-1/Ckit antibodies and finally gate them in the CD34 negative subset.

Table 1 shows that among 109 clones from 3 mice, 92.7% of the CD34−LKS cells were of p18−/− origin. See Table 1, bottom line. Therefore, the p18−/− genotype sustains its predominant representation in the HSC pool through nearly two years of serial competitive bone marrow transplant without apparent exhaustion. These results were also confirmed by LTC-IC yield from an independent serial transplantation experiment (data not shown). The absence of p18 provides a capacity for increased self-renewal not seen in the absence of the CKI p21 or p27.

Growth advantage of p18−/− CD34−LKS cells over their wild type counterparts in the competitive repopulation models suggests a possible expansion of HSCs in the p18−/− non-transplanted mice under homeostatic conditions. This possibility was examined with the phenotypic analysis between litter mate or age matched p18+/+ and p18−/− mice with the HSC phenotype, CD34−LKS. Our results are shown in FIG. 3.

FIG. 3 shows the enlarged pool size of HSCs in p18−/− mice under steady-state conditions and enhanced regeneration of p18−/− HSCs following the HSC transplantation.

FIG. 3a shows phenotypic quantitation of HSCs. Bone marrow nucleated cells from p18−/− mice (8-12 weeks) and gender matched p18+/+ mice were analyzed by flow cytometry (n=9). HSCs that are negative for lineage markers and CD34, positive for c-Kit and Sca-1, are referred to as "CD34−LKS" cells (see FIG. 17).

FIG. 3b shows repopulating potential of HSCs with limiting dilutions. Different numbers (10, 20 or 40) of CD34−LKS cells (CD45.2$^+$) were mixed with $10^5$ Sca-1 depleted competitor bone marrow cells (CD45.1$^+$/CD45.2$^+$) and injected into lethally irradiated recipients (CD45.1) (n=10 mice per cell dose). Different lineages in the peripheral blood were analyzed 5 and 14 weeks after transplantation. A level of 2.5% or higher of CD45.2$^+$ cells associated with multilineage differentiation was defined as positive engraftment in a given animal. CRU values were calculated with the software L-Calc (StemCell Technologies). The graph shows the difference of CRU values at 5 weeks (5 W) and 14 weeks (14 W).

FIG. 3c shows repopulating ability in the recipients transplanted with a higher dose of HSCs. Eighty CD34−LKS cells were co-transplanted with $10^5$ Sca-1 depleted competitor bone marrow cells into lethally irradiated recipients (n=5). The graph indicates the repopulating ability of the test cells as determined by the ratios of CD45.2 to CD45.1/CD45.2 cells in blood at week 5 (5 W) and 14 (14 W) after transplantation. FIG. 3d shows multi-lineage differentiation Profile. Multi-lineage differentiation was examined by using 6-color flow cytometric analysis. "GM", "T" and "B" indicate lineages for myeloid cell (Gr-1$^+$ and Mac-1$^+$), T cell (CD3$^+$) and B cell (B220$^+$) respectively.

FIG. 3a shows that we observed a 2-fold increase in frequency and 3-fold increase in absolute yield per marrow harvest of the CD34−LKS cells in the p18−/− mouse. In contrast, the more mature Lin−c-kit$^+$Sca-1$^-$ (LKS$^-$) cells, which are devoid of HSC activity but contain committed HPC subsets, had an insignificant change in frequency. Therefore HSC, but not HPC populations appeared to be increased in the absence of p18.

Figure 18:
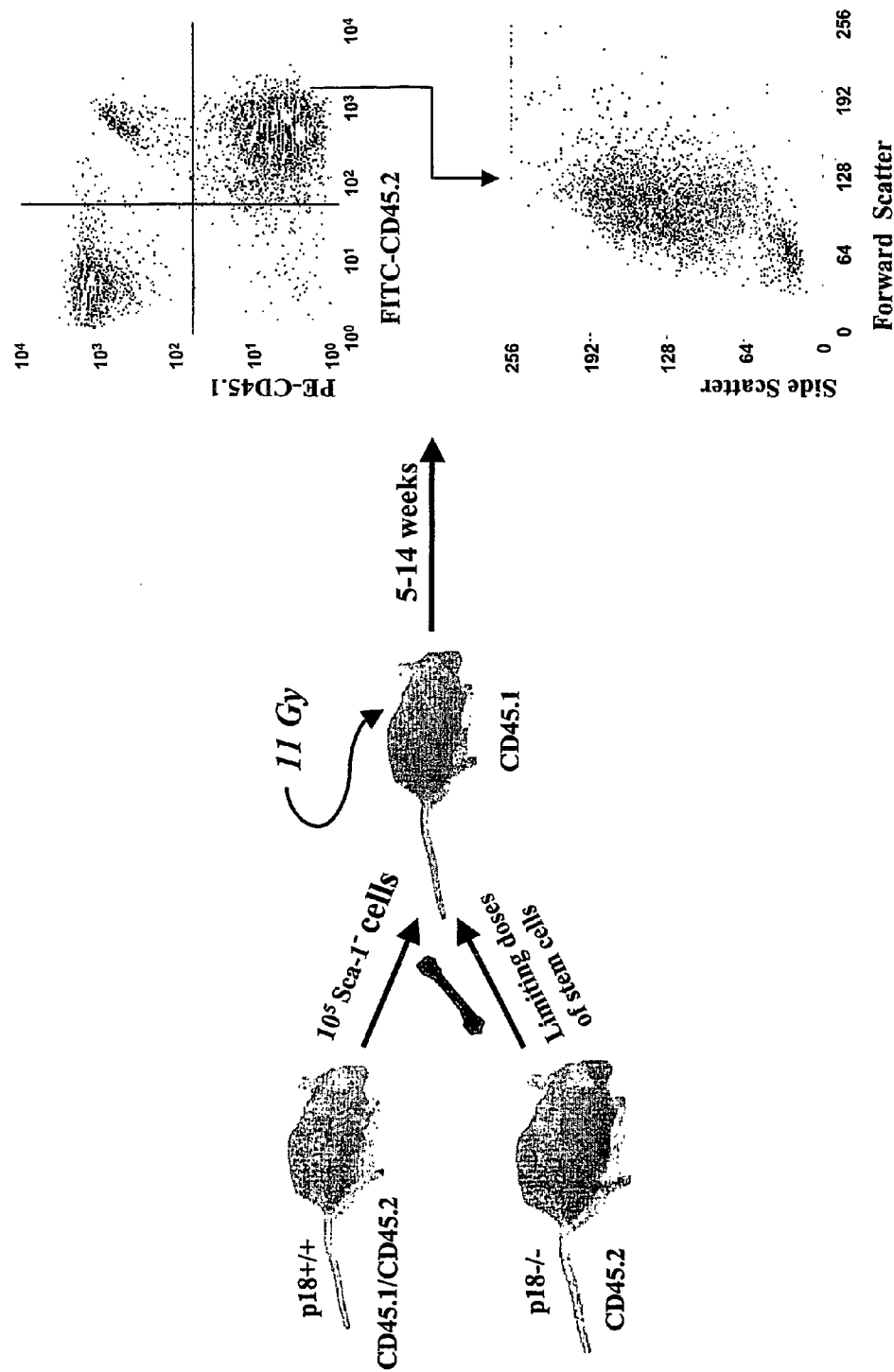
FIG. 18 shows the assay for vigorously testing the stem cell function, namely the competitive repopulation unit (CRU).

A 2-fold increase of HSC frequency (CD34−LKS) in p18−/− bone marrow was thought to be insufficient to account for the dramatic engrafting advantage of the p18−/− cells over the p18+/+ cells following the subsequent competitive bone marrow transplant (FIG. 1b and FIG. 2a). Rather, ongoing regeneration of 18−/− HSCs after transplantation was considered more likely. However, to further define this issue, we performed stem cell transplantation with CD34−LKS cells to assay the competitive repopulation units (CRU) with limiting dilution analysis (10, 20 or 40 CD34−LKS cells/mouse and 10 mice/dose). The original C57BL/6; 129/Sv strain was backcrossed into the pure C57BL/6L-Ly5.2 (CD45.2) background for 10 generations allowing us to accomplish the experiment in congenic mouse strains (see FIG. 18).

We examined CRU frequency in CD34−LKS cells at both week 5 and 14 after transplantation. Interestingly, while CRU frequency slightly increased from 1/22 to 1/14 in p18+/+ CD34− LKS cells, it substantially increased from 1/12 to 1/4 in p18−/− CD34−LKS cells (FIG. 3b). Normalized for the frequency and yield of CD34−LKS cells in the marrow, there was approximately a 7-fold increase in frequency and a 10-fold increase in absolute yield (2 femurs and 2 tibias) of CRU in the p18−/− bone marrow at 14 weeks post-transplant. The difference as assessed by CRU assay was in agreement with the data obtained from the mice injected with a higher dose of 80 CD34−LKS cells per mouse (FIG. 3c). There was also a 7-fold increase of relative engraftment level as compared to competitor cells in p18−/− groups at 3 months post-transplant without apparent alteration in lineage differentiation ratios (FIG. 3d). These data concur with the 14-fold increase in p18−/− LTRA by the competitive bone marrow transplant model shown in FIG. 1b, if normalized for the 2-fold increase of CD34−LKS cells in the unfractioned marrow. See FIG. 3a, left column.

Taking together the selective increase of CD34−LKS cells that was not observed in the more mature LKS$^-$ cells (FIG. 3a) and the apparent self-renewal of CRU seen in CD34−LKS cells (FIG. 3b), suggested a specific effect of p18 on HSCs. To directly address this issue, we measured cell divisions in distinct immunophenotypically defined cell populations among donor cells in irradiated recipients after bone marrow transplantation (BMT). The dye, 5- (and 6-) carboxy fluorescein diacetate succinimidyl ester (CFSE), was used to label the donor cells prior to tail injection and surface markers for HSCs and HPCs were applied to co-stain the marrow cells harvested 2 days after BMT. The number of initial cell divisions was measured based on the intensity of CFSE in each cell population in the recipients.

Within 3 cell divisions detected in the experiment, there was a significant increase of the cells that divided and retained the same phenotype in both p18−/− Lin−Sca-1$^+$ and p18−/− Lin−Sca-1$^-$ parent populations compared with the p18+/+ controls (measured as "precursor frequency" in flow cytometry). However, among the p18−/− cells, the increase of cell division seen in the more primitive Lin−Sca-1$^+$ cell subset was markedly more (approximately 2-fold more) than that seen in the more mature Lin−Sca-1$^-$ cell subset. Our data is shown in FIG. 4.

Figure 4:
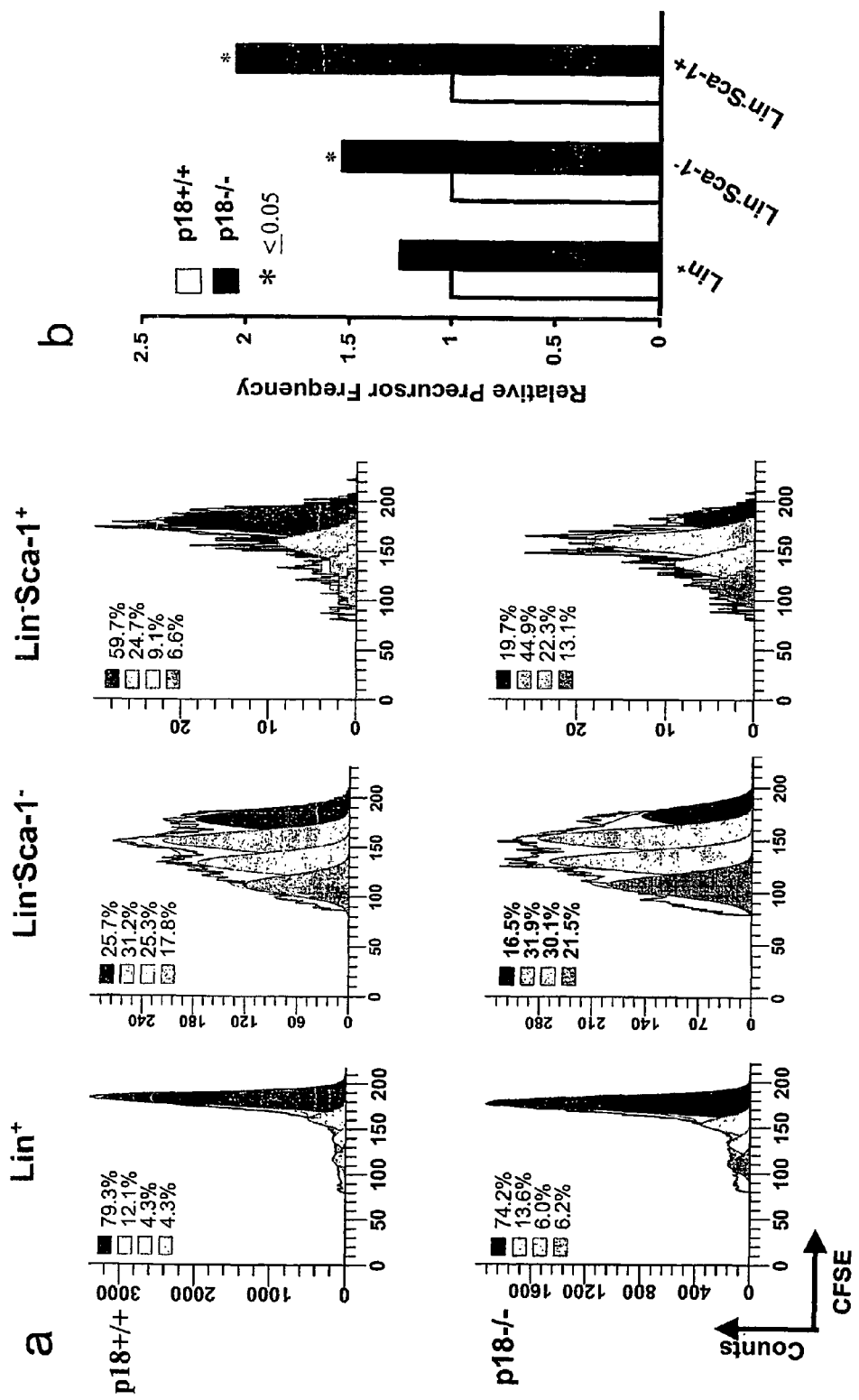
FIG. 4a demonstrates a level of cell division for p18+/+ cells compared to p18−/− cells.
FIG. 4b demonstrates the relative precursor frequency for Lin+, Lin-Sca-1−, and Lin-Sca-1+ cells in p18+/+ mice compared to p18−/− mice.

FIG. 4 shows a direct demonstration of increased divisions of the p18−/− HSCs in vivo. Bone marrow cells were labeled with CFSE, injected into lethally irradiated recipient mice and harvested at 2 days after the transplantation for assessing the number of cell divisions. Cells were stained with the lineage and stem cell markers described in the methods. CFSE labeled cells were analyzed in the gate for a specific phenotype.

FIG. 4a shows a representative figure of the flow cytometric analysis. The blue peaks on the right indicate undivided cells (parent cells) and each peak towards left side represents one cell division or generation. The percentages of the cells in each division obtained in a representative experiment are inserted in the graphs. The figure shown is from one of 4 experiments with similar results.

FIG. 4b shows a summary of the mean values from 4 independent experiments. An assumption made in the computation model is that cell number will double as cells proliferate through each daughter generation in a given population (Lin$^+$ vs. Lin−Sca-1$^-$ vs. Lin−Sca-1$^+$). The ModFit LT software was used to calculate "precursor frequency" as the proportion of the total cells calculated to have been present at the start of the experiment (derived by back-calculation according to the model) which have then gone on to true proliferation during the course of cell division. Data shown are the ratios of the precursor frequency between p18−/− and p18+/+ cell populations (4 experiments, 3-5 donor mice/each genotype in each experiment).

Therefore, FIG. 4 shows that depletion of p18 does not result in a generalized increase in cell proliferation of different lineages. Rather, the absence of p18 preferentially affects divisions of the more primitive cells, resulting in improved HSC self-renewal.

Figure 5:
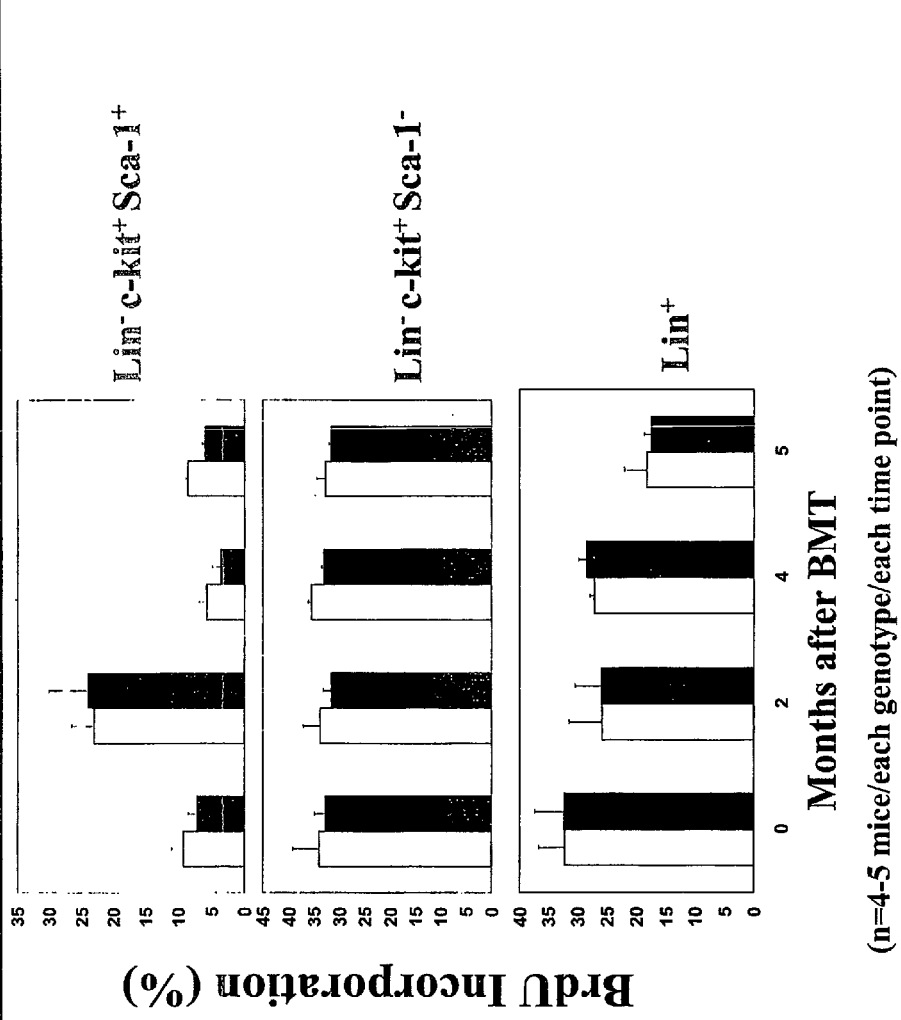
FIG. 5 shows graphs measuring BrdU incorporation into cell types having three different maturities in vivo (undifferentiated stem cells, intermediate cells and fully-differentiated cells).

FIG. 5 shows graphs measuring BrdU incorporation. To assess the cell cycling status in different hematopoietic subsets in vivo, either transplanted or non-transplanted mice were pulsed with a single dose of bromodeoxyuridine (BrdU) and mice were sacrificed in the second day for assessing the BrdU incorporation in conjunction with different hematopoietic markers. We found that there was no difference of BrdU incorporation in the hematopoietic cell subsets between p18−/− and p18+/+ groups. While we could not definitively document the difference at the true stem cell level in a most stringent term, our data suggest no overwhelming increase of cell proliferation in the stem cell progenies in the p18−/− marrow.

Figure 6:
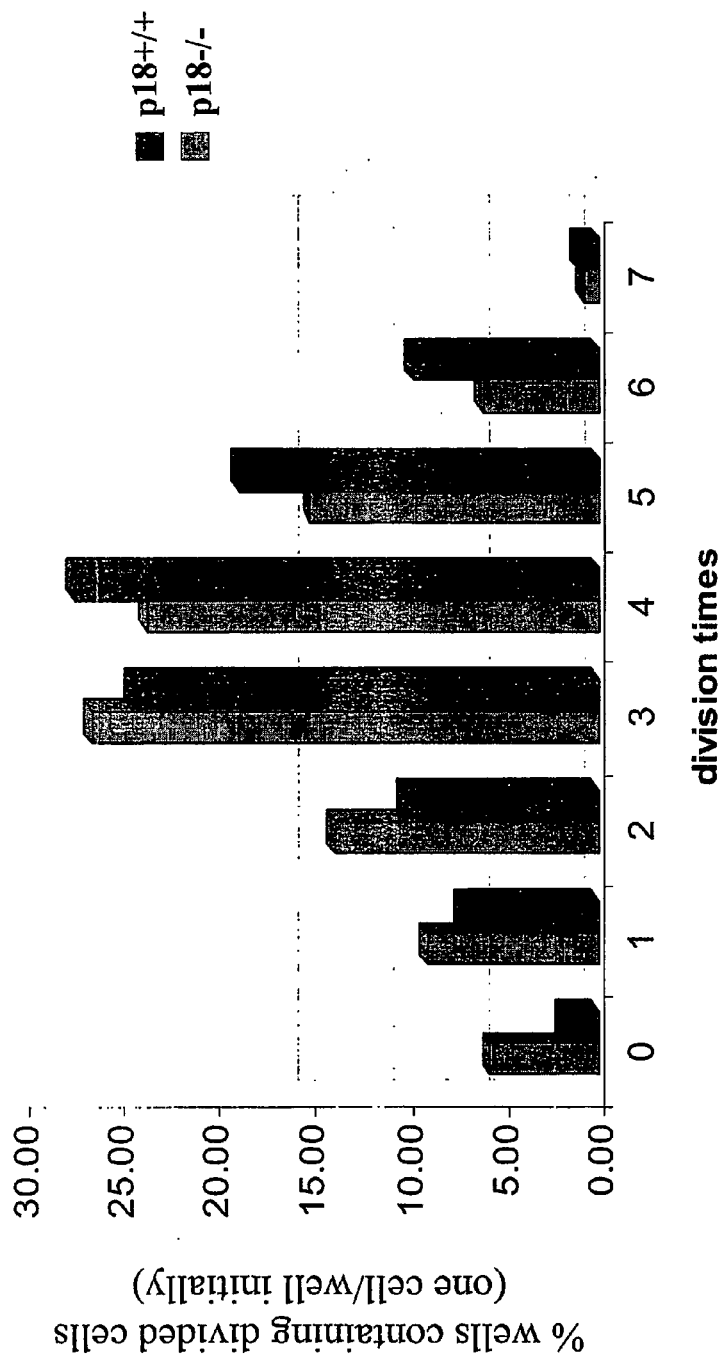
FIGS. 6, 7 and 8 show proliferative rates of the single stem or progenitor cell in vitro. Together with FIG. 5, these data support the notion that symmetric stem cell divisions but not the non-specific increase of cell proliferation can be promoted by deleting p18 protein.
Figure 7:
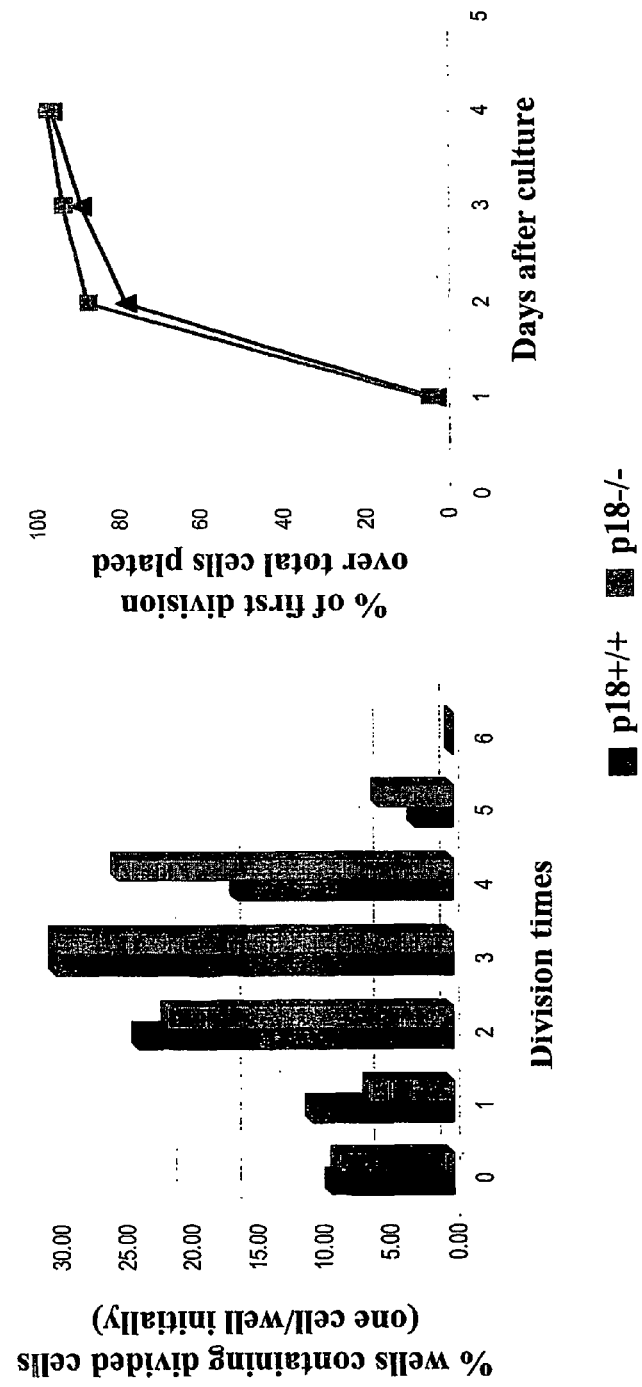
Figure 8:
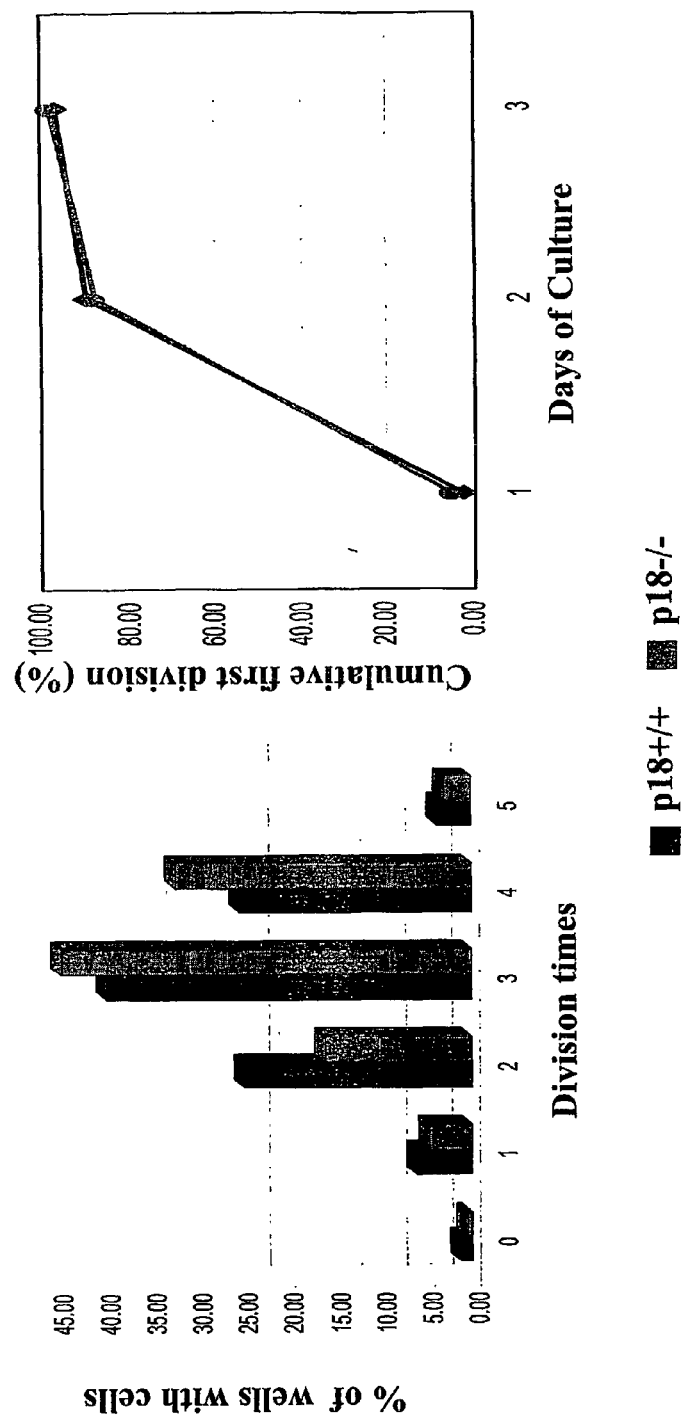

FIGS. 6, 7 and 8 show proliferative rates of the single stem or progenitor cell in vitro. To further assess the stem cell proliferation in at single cell level, we examined in vitro cell divisions of the CD34$^-$Lin$^-$c-Kit$^+$Sca-1$^+$ (CD34LKS) or Lin$^-$c-Kit$^+$Sca-1$^+$ (LKS) cells. Single CD34$^-$LKS or LKS cells were deposited to Terasaki plates (one cell/well) and cultured in serum free medium supplemented with SCF, Flt3L and TPO. While most cells entered cell cycle within 3 days, which was in agreement with previous studies by others, surprisingly, there was no significant difference in the rate of cell division between p18−/− and p18+/+ CD34$^-$LKS cells, neither in the LKS cells (>100 cells/cell type/experiment, 5 experiments in total). Further, there was also no difference in the rate of the first cell division of the CD34$^-$LKS cells. These indicate that p18 deficiency does not increase the proliferative rate of HSC, rather modulates the fate choice of HSC toward symmetric cell divisions. While one might still argue for the possibility of contamination of the progenitor cells in the immuophenotypes especially the LKS population, our data strongly demonstrate no substantial increase of proliferative rate in the progenitor cell pools.

Figure 9:
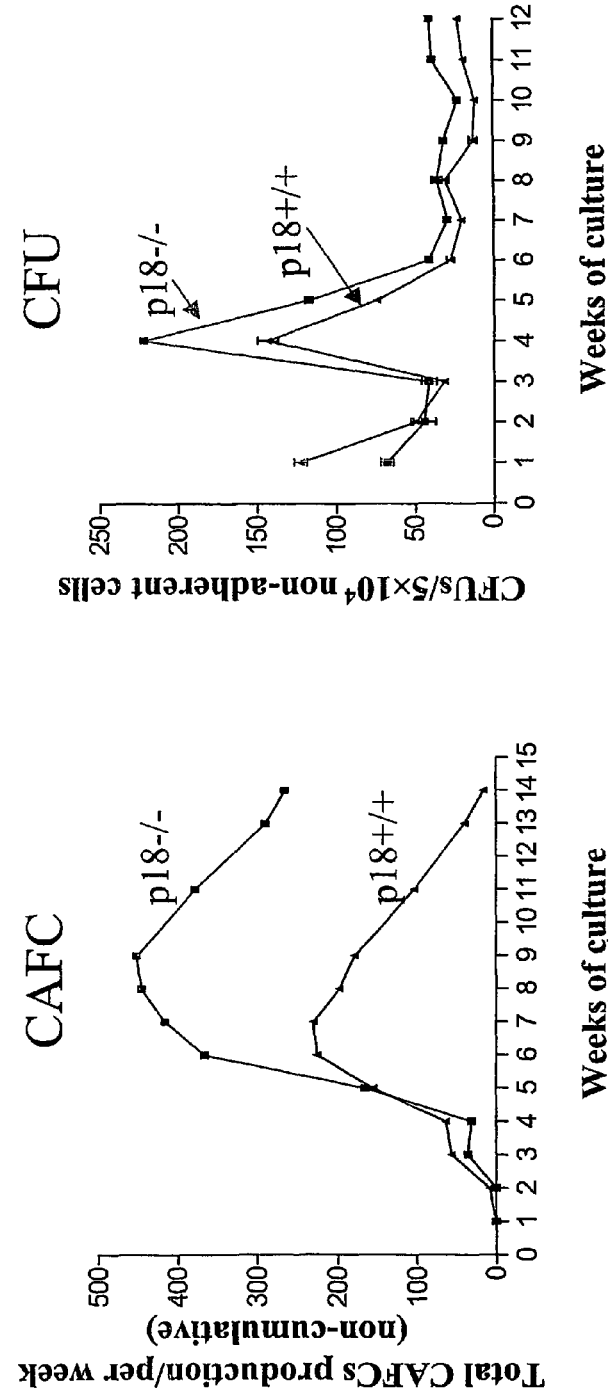
FIG. 9 shows the selective expansion of cobblestone area forming cells ("CAFC") (an in vitro surrogate assay for stem cells) during long-term culture. Based on the in vivo data (FIG. 1-5), down-modulating p18 may permit enhanced stem cell expansion in vitro, a hypothesis that has been tested in our laboratory with this data together with the data in FIG. 10 below.
Figure 10:
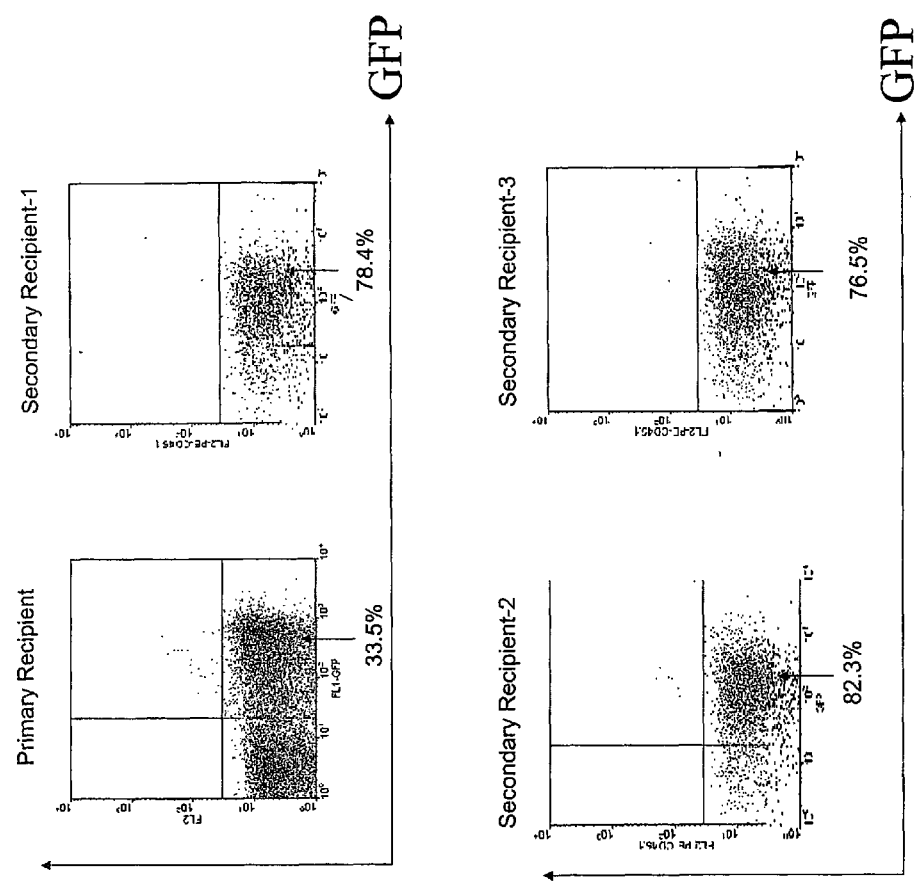
FIG. 10 shows the long-term engraftment of the p18−/− stem cells after 19 weeks in vitro. To further demonstrate the in vivo reconstituting ability of cells that had been cultured under the Dexter culture condition for 19 weeks (FIG. 9), 2-20×10$^5$ cells with non-adherent and adherent populations were transplanted into lethally irradiated hosts. Three of 7 mice revealed long-term engraftment in the p18−/− transplanted group (0.5-33% engraftment levels); while there was no engraftment in the p18+/+ group (n=7). Moreover, a substantial level (38.6% on average) of long-term engraftments (0.7 months) in multilineage was achieved in secondary recipients transplanted with the p18−/− cells (n=3), demonstrating the self-renewal potential of the expanded HSCs after the extended period of long-term culture. The green fluorescent protein (GFP) positive cells are the cells that have been transplanted into the recipients. These data strongly indicate that p18 absence is able to substantially mitigate the differentiating effect of the ex vivo culture conditions on HSCs, and therefore offer a strong rationale for targeting p18 in human HSC expansion.

FIG. 9 shows the selective expansion of CAFC during long-term culture. To demonstrate whether increased stem cell self-renewal may be readily achieved in vitro due to the absence of p18, we performed the Dexter long-term culture of bone marrow cells to enumerate the CAFC. There was no difference of CAFC yield in the first 4 weeks of the long-term culture between p18−/− and p18+/+ flasks. However, significantly more CAFCs were constantly generated in p18−/− than in p18+/+ flasks (n=4) from 6 weeks to 19 weeks after the initial culture. Strikingly, the frequency of CAFC at week 19 in p18−/− culture was still equivalent to its level at week 5, whereas the p18+/+ culture nearly lost its ability of producing CAFCs at week 19. In contrast, there wan no apparent difference of CFU at day 7 (an in vitro assay for hematopoietic progenitors) frequency between these two groups. It should be noted that CAFC has been extensively demonstrated by others to be correlated with the long-term repopulating stem cell activity in vivo in mouse models.

EXAMPLES

To compile the aforementioned data and confirm the operability of my concept, we have done the following experiments.

Example 1

Obtain p18+/+ and −/− Mice p18+/− mice in a C57BL/6; 129/Sv background were imported from the laboratory of David Franklin at Purdue University. p18−/− or +/+ mice were generated from p18+/− breeding pairs. Mouse colonies were maintained in the certified animal facility at University of Pittsburgh Cancer institute. Mice were genotyped by a PCR approach using the tail DNA (primers described below). Littermates or age-matched mice (8-12 weeks) were used in competitive bone marrow transplantation and stem cell phenotypic analysis.

For transplantation with purified stem cells and CRU analysis, the mice with the mixed background were bred back into C57BL/6-Ly5.2 (CD45.2) background for 10 generations. Wild type recipients in a C57BL/6129 background for BMT and mice with a B6.SJL-Ly5.1 (CD45.1) congenic background were purchased from the Jackson laboratory (Bar Harbor, Me.). All the procedures involved in the mouse work were approved by the Institutional Animal Care and Use Committee at the University of Pittsburgh.

Example 2

Competitive Bone Marrow Transplantation

Equal numbers of bone marrow nucleated cells ($2 \times 10^6$ each) from p18+/+ and p18−/− mice were mixed and transplanted into the recipients which were treated with 10 Gy whole-body irradiation at the rate of 5.96 Gy/min or 0.94 Gy/min depending on the configuration of a specific $^{137}$Cesium irradiator used in different experiments.

To perform the secondary competitive bone marrow transplant, bone marrow cells were harvested from the mice at 10 months after the primary competitive bone marrow transplant, mixed with freshly isolated wild type bone marrow cells (non-transplanted cells from mice at age of 8 weeks) at a 1:1 ratio and secondarily transplanted into new lethally irradiated wild-type recipients (age of 8 weeks). Blood from the transplanted mice was collected at different time points for genotypic analysis with the semi-quantitative PCR method. At varied time points after the primary or secondary competitive bone marrow transplant, some mice were sacrificed and bone marrow nucleated cells were used for genotypic analysis in different lineages and HSC or HPC compartments involving the single cell or colony assays.

The results of this is shown in FIG. 1. FIG. 1 shows preferential outgrowth of p18−/− hematopoietic cells during long-term engraftment after primary competitive bone marrow transplant. Bone marrow cells from p18−/− and p18+/+ mice were mixed with a 1:1 ratio and injected into lethally irradiated recipient mice ($4 \times 10^6$ cells in total per mouse). Semi-quantitative PCR was performed at different time points to determine the contribution of each genotype to the hematopoietic reconstitution after competitive bone marrow transplant. FIG. 1a shows standardization based on the correlation between the relative density of p18−/− signal in total for each lane on the gel and the actual ratio of the two cell populations. FIG. 1b shows representative data for blood cells at 7 months after competitive bone marrow transplant. FIG. 1b, columns numbered 1 to 7 indicate the seven individual recipient mice used. According to the standardization, the converted percentages of p18−/− cells in the blood were shown below the PCR gel.

Example 3

Semi-Quantitative PCR and Single-Colony PCR

The contribution of p18+/+ or p18−/− cells was determined by semi-quantitative PCR with the following 3 primers:

```
p18WT-F      (5'-AGCCATCAAATTTATTCATGTTGCAGG-3')
P18MG-47-R   (5'-CCTCCATCAGGCTAATGACC-3')
PGKNEO-R     (5'-CCAGCCTCTGAGCCCAGAAAGCGAAGG-3')
```

The spleen cells from p18+/+ and p18−/− mice were mixed at different ratios for standardization of the PCR reaction. For single colony PCR, individual colonies were picked up with micromanipulation and lysed in 1×PCR buffer containing 2.5 mM $MgCl_2$ and 100 μg/ml Proteinase K for 1 hour at 60° C., followed by inactivation of the reaction for 20 min at 95° C.

Example 4

CFC and LTC-IC Cultures

Bone marrow cells were placed in the defined methycellulose medium M3434 (StemCell Technologies) and plated in 24-well plates. The CFC colonies were then scored at day 7-14 under an inverted microscope, picked up and assayed for the p18 genotype with PCR. Long-term culture with limiting dilution was performed as previously described. Briefly, the unfractioned bone marrow cells were plated on an irradiated (15Gy) primary mouse stromal monolayer in 96-well plates containing 150 μl of M5300 medium (Stem Cell Technologies) supplemented with $10^{-6}$ M hydrocortisone. Sufficient wells at the limiting dose of approximately one long-term culture-initiating cell (LTC-IC) per well were included. The medium was changed with half fresh medium weekly and the long-term culture at week 5 was overlaid with 100 μl of M3434 (Stem Cell Technologies). The plates were evaluated for the presence of CFC colonies at 10 days. The colonies were microisolated and followed by PCR analysis for the p18 genotype.

Example 5

Flow Cytometric Analysis

For stem cell quantitation, the bone marrow nucleated cells were stained with a mixture of biotinylated antibodies against mouse CD3, CD4, CD8, B220, Gr-1, Mac-1 and TER-119 (Caltag), lien co-stained with streptavidin-PE-Cy7, anti-Sca-1-PE, anti-c-Kit-APC and anti-CD34-FITC (BD PharMingen). Propidium iodide was used for dead cell discrimination. A MoFlo High-Speed Cell Sorter (DakoCytomation) and the Summit software (version 3.1, DakoCytomation) were used for data acquisition and analysis. For lineage phenotype analysis, 50 μl of the blood was stained with either anti-CD3-PE and anti-B220-FITC or anti-MAC-1-PE and anti-Gr-1-FITC. The red cells were lysed with FACS Lysing Solution (BD Biosciences) and analyzed by the Beckman-Coulter XL cytometer.

Example 6

Single Stem Cell Sorting and Culture

The Sca-1+ cells were isolated from bone marrow cells using the EasySpe kit according to the manufacturer's protocol (StemCell Technologies) and then stained with a mixture of lineage-specific antibodies listed above, anti-c-kit-APC and anti-CD34-FITC. LKS or CD34−LKS cells were sorted into 384-well plates (Nunc) at one cell per well using the MoFlo High-Speed Cell Sorter with subsystems of CyCLONE Automated Cloner and SortMaster Droplet Control. Each well contained 50 μl of IMDM supplemented with 50 ng/ml of Flt3 ligand (Flt3-L), 50 ng/ml of SCF and 10 ng/ml of TPO. After culture for 14 days, the morphology of each colony was examined under a microscope and the colonies were lysed for PCR.

Example 7

Stem Cell Transplantation with Limiting Dilution Analysis

Sorted CD34−LKS cells from p18−/− mice in the background of C57BL/6 (CD45.2) were used for measuring the competitive repopulating unit (CRU). CD34−LKS cells at a limiting dose (40, 20 or 10 cells/mouse) were mixed with $1 \times 10^5$ Sca-1-depleted bone marrow cells from F1 mice of C57BL/6 and B6.SJL (CD45.1+ and CD45.2+). The cell suspension was injected through tails into B6.SJL (CD45.1+) mice that were irradiated at a fractioned dose of 11Gy. Ten recipients were included for each group at each dose. Blood cells from the recipients were stained with PE-CD45.1 and FITC-CD45.2 to determine engraftment level of donor cells after transplantation. 2.5% or higher of CD45+ cells containing granulocytes, monocytes and lymphocytes was defined as positive engraftment in a given animal. The Beckman-Coulter XL cytometer was used for data acquisition. Based on the Poisson distribution of the negatively engrafted mice, CRU values were calculated with the software L-Calc (StemCell Technologies) and plotted in a graph. Animals that died during the course were not counted in the limiting dilution analysis. As an independent test to determine the engraftment levels, additional 5 recipient animals for each group were transplanted with a higher dose of CD34−LKS cells (80 cells/mouse).

Example 8

In Vivo Assay for Tracking Cell Divisions

Bone marrow cells were labeled with one μM of CFSE (Molecular Probes) as described. $1 \times 10^8$ CFSE labeled p18+/+ or p18−/− bone marrow cells were injected into a lethally irradiated mouse. Two days after transplantation, recipient marrow cells were stained with the antibody cocktail for lineage markers, Sca-1 and c-Kit. MoFlo High-Speed Cell Sorter was used for data acquisition and the ModFit LT software (Version 3.0, Verity Software House) was used for cell proliferation analysis.

Statistical Analysis

The student's t test was used to analyze the statistical differences between p18−/− and p18+/+ groups with the p values indicated in the related graphs.

Summary

While both p21 and p18 appear to affect cycling kinetics in primitive cells, they have very distinct phenotypes: p21−/− stem cells undergo premature exhaustion, while p18−/− stem cells self-renew. Without overwhelmingly non-specific proliferation in other cell populations, increased regeneration of p18−/− HSCs suggests that the balance of differentiation to self-renewal in the absence of p18 favors self-renewal. This notion is indirectly supported by the data from others demonstrating that p18 expressing cells have an increase in asymmetric division. It is believed that critical decisions of cell fate are made during the G1-phase. Upon mitogenic stimuli, cyclin D is upregulated and interacts with CDK4/6, resulting in Rb phosphorylation to initiate cell cycle progression. White Cip/Kip proteins (such as p21) broadly inhibit CDK2 in late G1/S and possibly CDK1 in M phase, they are not capable of inhibiting CDK4/6 activity early in G1. In contrast, INK4 proteins (such as p18) are able to specifically compete with cyclin D to bind CDK4/6 in early G1. Given the distinct effects of these two CKI families in stem cell regulation, we propose a model in which modulation of a distinct CKI or its class at a specific position of the cell cycle may be an important mechanism for balancing self-renewal and differentiation in stem cells. Down modulating p18 may permit enhanced stem cell expansion, a hypothesis that can now be tested in adult cells.

While I have discussed various specific examples in some detail above, one of skill in the art could, with the teachings here, readily develop alternative solutions. Thus, I intend the coverage of my patent to be defined not by the specific abstract nor examples discussed here, but rather by the appended claims and their legal equivalents.

In the claims, I use certain terms in specific ways. For example, the singular allows for more than one (e.g., the claim phrase, "a compound selected from the group consisting of A, B and C" covers a composition with at least one—and perhaps two or more—of the enumerated compounds).

I use the claim term "symmetrically self-renewing population" to encompass both in vitro cell culture and in vivo culture as, for example, a therapeutic or experimental implant.

I use the claim term "human-compatible" to mean able to be survivably-implanted in a human. This may be done by, for example, using a non-immunogenic cell line which will provoke little or no immune response, or by the conjoint administration to the human patient of an immunosuppressant pharmaceutical to suppress the immune response to the stem cell implant. A non-immunogenetic cell line may be, for example, the patient's own stem cells, extracted from the patient and cultured ex vivo for autologous delivery back to the patient.

I use the term "intracellular environment" to mean the intracellular environment of the stem cell culture. I use the term "substantially free" to mean an amount less than the amount which would materially inhibit cell line regeneration. One may control the intracellular environment by, for example, limiting expression of the p18 protein; this may be done by deleting or mutating the p18 gene (to make a p18−/− genotype cell) or its promoter (to make a p18− phenotype cell), or by downregulating the gene promoter, or by providing a compound capable of binding and thus neutralizing the p18 protein. One known approach to down-regulating gene expression is inhibiting expression of p18 by using "RNA interference," that is, using small interfering RNA or RNA-directed gene silencing. I do not imply any unstated temporal limitation on this; thus, for example, I intend my claims to cover transient downregulation of p18 transcription, or transient binding or enzymatic lysis of the p18 protein, such that the cells may revert to a p18+ phenotype once the p18-inhibiting factor is removed.

In the claims, I use the term "p18" to mean the polypeptide as known in the art (see supra), but also any mutation of it which differs from it insubstantially. Thus, for example, a wild-type variant or mutant which, despite its nominal difference from the published sequence for p18, achieves a similar function of impeding a cell line's regenerative capacity, is considered "p18" for the claims appended.

A Change of p18 expression level or a block of p18 function in cell lines can be used to screen potential drug candidates for stem cell renewal, to assay the effectiveness of potential drug candidates on p18+ and p18− cells. Thus, in the claims, I use the term "candidate composition" to mean a composition of matter which is a candidate for some kind of therapeutic use; it can be a small organic chemical, for example, or a polypeptide.

Background—In April 2003, Dr. Tao Cheng disclosed a method of extending the self-renewal of murine hematopoietic stem cells by elimination of the CDK inhibitor p18. The technology was returned to him in October, and he personally filed a provisional patent based on a manuscript he had submitted for publication (it was published in Nature Cell Biology in May 2004). Dr. Cheng has now made a significant advance in this technology—he has achieved the same enhancement of self-renewal in human hematopoietic stem cells by transiently blocking p18 expression with siRNA. He is submitting an update to OTM to ask for reconsideration based on this new development.

Technology Summary—While embryonic stem cells can be maintained indefinitely in an undifferentiated state in culture, adult-derived stem cells typically do not display the same property of self-renewal. In fact, the biggest hurdle to the use of adult-derived stem cells is the difficulty in expanding the undifferentiated cell population in vitro. In particular, hematopoietic stem cells (HSCs) are rapidly depleted in culture—a recent report states it has "not yet been possible to identify a distinct hematopoietic stem cell with the capacity of self-renewal and in-vivo reconstitution of hematopoiesis" (*Cell Therapy: Technologies, Companies and Markets*, May 2004).

Dr. Cheng has shown that p18 deficient murine HSCs show dramatically improved self-renewal in vitro as compared with wild type HSCs. This is apparently accomplished not by increasing the rate of cell division, but by postponing differentiation of the cell. Not only were the HSCs able to maintain an undifferentiated state for a longer period of time in culture, they demonstrated a remarkable engraftment advantage, with a 14-fold greater abundance of long-term repopulating ability than wild type HSCs in irradiated mice. The dominance of the p18 deficient phenotype was observed in all major blood cell types, indicating multilineage differentiation, even in secondary recipients.

Recently, Dr. Cheng was able to demonstrate the same effect in human CD34 cells. He identified expression of the p18 protein in human HSCs and then used a targeted siRNA to reduce its expression. Using two different methods to deliver the siRNA to the cell he was able to produce p18 deficient HSCs and to maintain the cells in vitro. He is currently examining the engraftment of these HSCs in NOD/SCID mice. Because of p18 expression is not unique to HSCs, it is anticipated that this approach could be used to enhance the in vitro expansion of other types of adult-derived stem cells as well.

Currently, the only known method of increasing HSC self-renewal is by genetically modifying the cell to express the exogenous gene, HOXB4. The current method provides advantages over the HOXB4 approach because it allows for transient disruption of p18 during in vitro expansion without the genetic manipulation of the cell. Such an approach is likely to be viewed more favorably from a regulatory perspective, as it minimizes the risk of unforeseen results from genetic manipulation, such as the development of leukemic transformation that was observed after transduction with HOXB8.

Requested Action—Under normal circumstances, OTM might reasonably wait for data from the SCID mouse experiments before making a decision to approve the current technology for patenting. However, because a provisional patent already exists, it will be necessary to take action prior to the filing deadline in October. If based on this new information, OTM decides that it wishes to approve the patent filing then the current data and the provisional would need to be combined in a full utility patent application. If OTM decides not to pursue patenting based on this information, Dr. Cheng requests that OTM release the new developments so that he may make arrangements for meeting the filing deadline on his own.

Ongoing Studies in Human Hematopoietic Stem Cells

Figure 11:
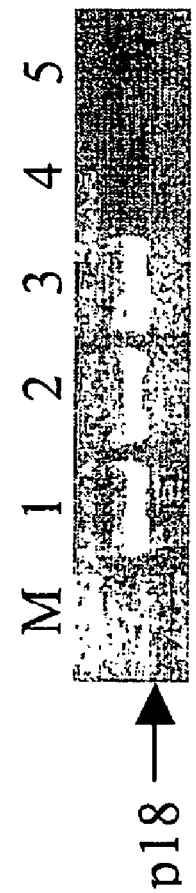
FIG. 11 shows gene expression of p18 in human hematopoietic stem cells by RT PCR method. M: molecular weight markers; 1-2: two duplicate samples of human stem cells from cord blood; 3: positive control from Hela cells; 4: negative control—no RT enzyme; 5: negative control—no mRNA template.
Figure 12:
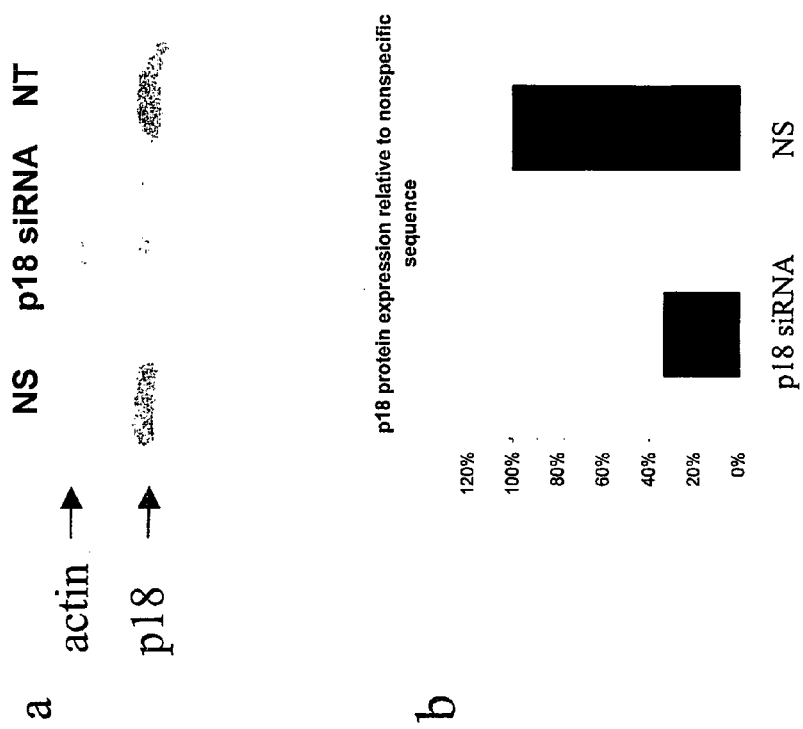
FIG. 12 shows that p18 protein in human stem cells can be substantially reduced by p18 RNA interference technique.
Figure 13:
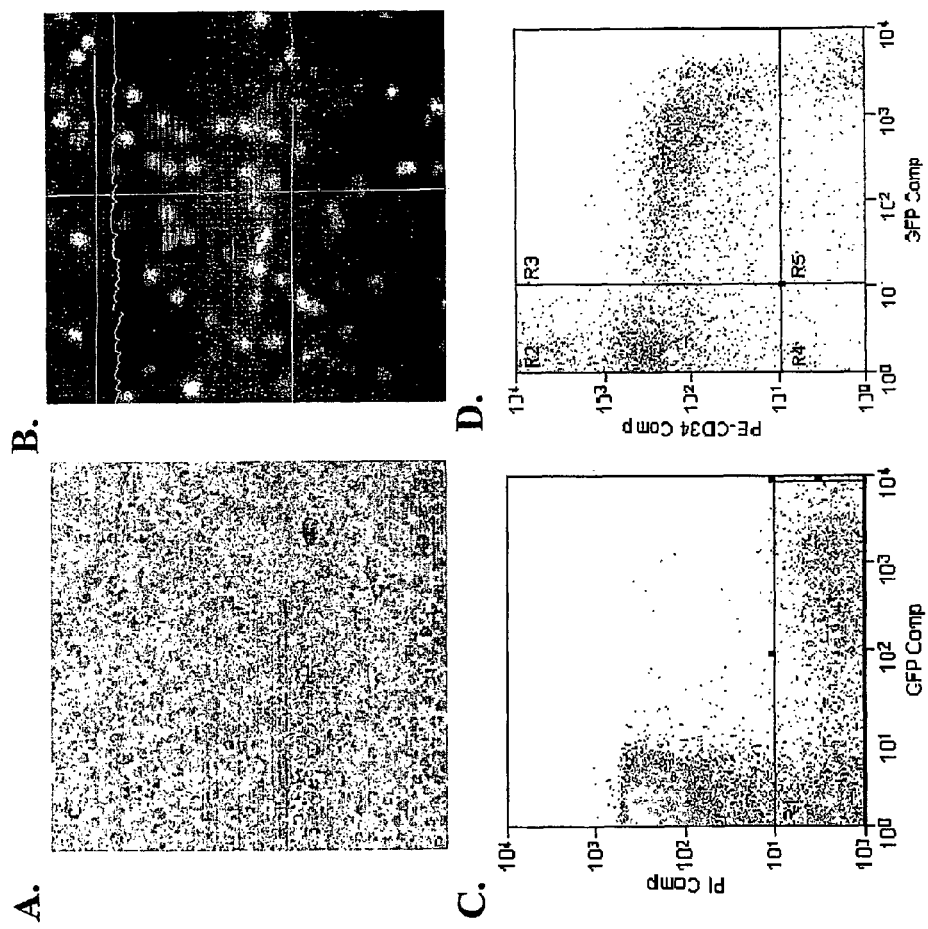
FIG. 13 shows the feasibility of delivering siRNA oligos into human stem cells by a high efficiency electroporation method. A & C: control cells without the electroporation method, B & D: test cells with p18 siRNA oligos conjugated with green fluorescence delivered by an optimized electroporation method. The upper panel is the direct visualization under a microscope, and the lower panel is the quantitative analysis by flow cytometry.
Figure 15:
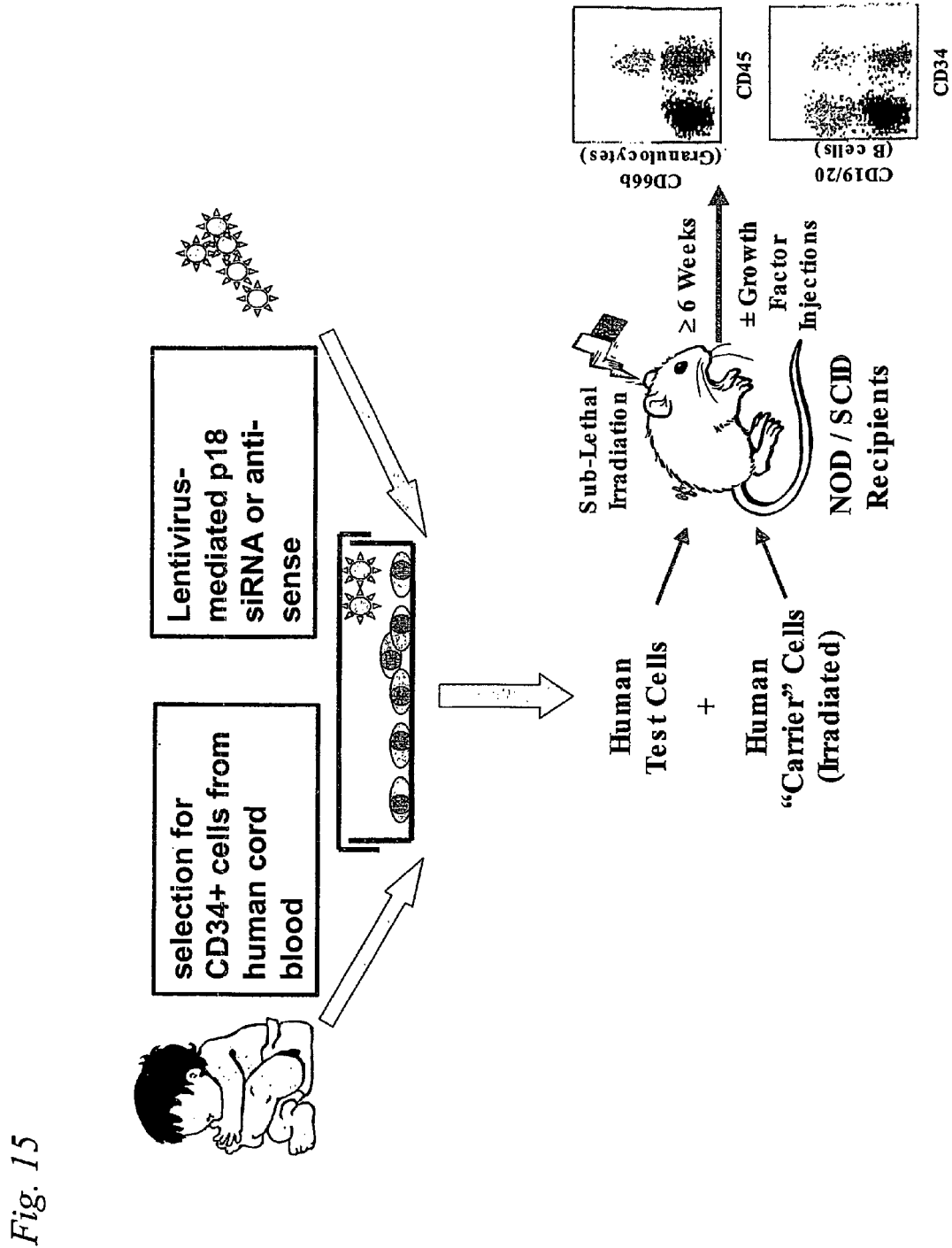
FIG. 15 shows a schematic experimental procedure for testing human stem cells deficient in p18 with an in vivo model.

To explore the potential applications of targeting p18 in human stem cell therapies, we have detected the expression of the p18 protein in human CD34 cells (FIG. 11) and defined an effective small RNA interfering sequence for knocking the p18 protein down in the human cells (FIG. 12). In addition, we have tried two approaches in delivering the siRNAs into human cells. One was the electroporation (FIG. 13) and another one is lentiviral vector (FIG. 14). With either method, we were able to achieve a considerable level of transduction in the human cells (more than 50%). A functional assessment after targeting p18 in human CD34 cells involving the use of NOD/SCID mice is currently under the way, (FIG. 15).

We claim:

1. A method of expanding a population of human hematopoietic stem cells by promoting self-renewal of the population of human hematopoietic stem cells comprising:
    delivering small RNA interfering sequences (siRNA) to the human hematopoietic stem cells for the reduction of p18 levels in the intracellular environment of the stem cells.
2. The method of claim 1, wherein said human hematopoietic stem cells are CD34+ cells.
3. The method of claim 1 further comprising implanting the siRNA treated human hematopoietic stem cells into a human.
4. The method of claim 3, wherein said siRNA treated human hematopoietic stem cells are CD34+ cells.
5. The method of claim 3, wherein the siRNA treated human hematopoietic stem cells contain no intracellular p18.
6. The method of claim 1, wherein the siRNA treated human hematopoietic stem cells contain no intracellular p18.
7. A method of stimulating self-renewal of a population of human hematopoietic stem cells by reducing intracellular levels of p18 comprising:
    delivering small RNA interfering sequences (siRNA) to the human hematopoietic stem cells by one of electroporation or lentiviral vector for the reduction of p18 levels in the intracellular environment of the stem cells.
8. The method of claim 7, wherein said human hematopoietic stem cells are CD34+ cells.
9. The method of claim 7, further comprising implanting the siRNA treated human hematopoietic stem cells into a human.
10. The method of claim 9, wherein said siRNA treated human hematopoietic stem cells are CD34+ cells.
11. The method of claim 9, wherein the siRNA treated human hematopoietic stem cells contain no intracellular p18.
12. The method of claim 7, wherein the siRNA treated human hematopoietic stem cells contain no intracellular p18.
13. A method of promoting self-renewal of a population of human hematopoietic stem cells comprising:
    expanding the population of human hematopoietic stem cells by delivering small RNA interfering sequences (siRNA) to the human hematopoietic stem cells for a reduction of p18 levels in the intracellular environment of the stem cells.
14. The method of claim 13, wherein said human hematopoietic stem cells are CD34+ cells.
15. The method of claim 13, wherein the siRNA treated human hematopoietic stem cells contain no intracellular p18.

* * * * *